US008762162B2

(12) United States Patent
Omori et al.

(10) Patent No.: US 8,762,162 B2
(45) Date of Patent: Jun. 24, 2014

(54) MEDICAL PRACTICE INFORMATION MANAGEMENT SYSTEM, MEDICAL PRACTICE OPERATION ASSISTANCE TERMINAL, MEDICAL PRACTICE INFORMATION MANAGEMENT METHOD, MEDICAL PRACTICE OPERATION ASSISTANCE METHOD, STORAGE MEDIA STORING MEDICAL PRACTICE INFORMATION MANAGEMENT PROGRAM AND STORAGE MEDIA STORING MEDICAL PRACTICE OPERATION ASSISTANCE PROGRAM

(75) Inventors: Shinichi Omori, Tokyo (JP); Tsuyoshi Nagaeda, Saitama (JP); Yasuyuki Fukuhara, Tokyo (JP)

(73) Assignee: Olympus Corporation (JP)

( * ) Notice: Subject to any disclaimer, the term of this patent is extended or adjusted under 35 U.S.C. 154(b) by 2406 days.

(21) Appl. No.: 11/192,239

(22) Filed: Jul. 28, 2005

(65) Prior Publication Data
US 2006/0026038 A1 Feb. 2, 2006

(30) Foreign Application Priority Data

Jul. 28, 2004 (JP) ................................. 2004-220268

(51) Int. Cl.
*G06Q 10/00* (2012.01)
*G06Q 50/00* (2012.01)
*G06Q 50/22* (2012.01)

(52) U.S. Cl.
CPC ..................................... *G06Q 50/22* (2013.01)
USPC .................................................. 705/2; 705/3

(58) Field of Classification Search
CPC ...................................................... G06Q 50/22
USPC ............................................................ 705/2, 3
See application file for complete search history.

(56) References Cited

U.S. PATENT DOCUMENTS 5,991,728 A * 11/1999 DeBusk et al. ................... 705/2
2001/0016821 A1 * 8/2001 DeBusk et al. ................... 705/2
(Continued)

FOREIGN PATENT DOCUMENTS

| JP | 11-154185 | 6/1999 |
| JP | 2001-142978 | 5/2001 |

(Continued)

OTHER PUBLICATIONS

Edmond, Charles V, "Chapter 7. Virtual Reality and Surgical Simulation" as found in "Computer-aided otorhinolaryngology: head and neck surgery" edited by Citardi, Martin J. 2002 Marcel Dekker.*

(Continued)

*Primary Examiner* — Neal Sereboff
(74) *Attorney, Agent, or Firm* — Ostrolenk Faber LLP

(57) ABSTRACT

A medical practice operation assistance terminal according to the present invention comprises a medical practice acquisition unit which is capable of transmitting an acquisition request of a medical practice to a data base storing information relating to medical practice(s), and acquiring the medical practice(s) related to the acquisition request; a judgment unit comparing identifier of the readout item of a medical practice and identifier of the item specified among the displayed items of the acquired medical practice(s); and an acquisition decision maker unit for deciding whether or not the medical practice acquisition unit is to be activated with the specified item as a search condition in accordance with a category of the specified item constituting the medical practice, if a readout identifier information identifies with the identifier information of the specified item.

23 Claims, 15 Drawing Sheets

(56) References Cited

U.S. PATENT DOCUMENTS

| | | | |
|---|---|---|---|
| 2003/0046109 | A1 | 3/2003 | Uchikubo |
| 2004/0167465 | A1* | 8/2004 | Mihai et al. .................. 604/67 |
| 2004/0172302 | A1* | 9/2004 | Martucci et al. ............... 705/2 |
| 2005/0038674 | A1* | 2/2005 | Braig et al. .................... 705/2 |

FOREIGN PATENT DOCUMENTS

| | | |
|---|---|---|
| JP | 2001-312566 | 11/2001 |
| JP | 2001-344338 | 12/2001 |
| JP | 2002-117144 | 4/2002 |
| JP | 2002252064 | 8/2002 |
| JP | 2003-099529 | 4/2003 |
| JP | 2003-225305 | 8/2003 |
| JP | 2004-110819 | 4/2004 |
| JP | 2004-110820 | 4/2004 |
| JP | 2004-348717 | 12/2004 |
| JP | 2005-115495 | 4/2005 |

OTHER PUBLICATIONS

Boehringer Laboratories—"Postoperative Orthopedic Autologous Transfusion Using the Boehringer Autovac TC Autotransfusion System—Sample Protocol" Apr. 1, 2004.*

Breanndan et al. "Ordering Blood for the Wrong Patient—Getting Inside the Minds of Ordering Physicians" Mayo Clinic Proce. 2003; 78:1337-1339.*

Japanese Office Action dated Oct. 20, 2009 in corresponding Japanese Patent Application No. 2004-220268 (in Japanese language).

Search report issued by European Patent Office on Sep. 12, 2005 in connection with corresponding European application No. EP 05 01 6301.

Medical Support System for Continuation of Care Based on XML Web Technology, Stalidis, et. al. *International Journal of Medical Informatics*, 64 (2001) 385-400; XP 4329225A.

Architecture for Networked Electronic Patient Record Systems, Takeda, et. al. *International Journal of Medical Informatics*, 64 (2001) 385-400; XP 4329225A.

Communication from the European Patent Office dated Apr. 26, 2007 in connection with corresponding European Application No. EP 05 016 301.

Choi et al., "MobileNurse: hand-held information system for point of nursing care" Jun. 2004, CMPB, Elsevier, vol. 74, pp. 245-254.

Rodriguez et al., "PDA vs. Laptop: A Comparison of Two Versions of a Nursing Documentation Application" CBMS 2003, Proceedings, IEEE.

Agarwal, et al., "On the Scalability of Data Synchronization Protocols for PDAs and Mobile Devices" Jul./Aug. 2002, IEEE Network, pp. 22-28.

* cited by examiner

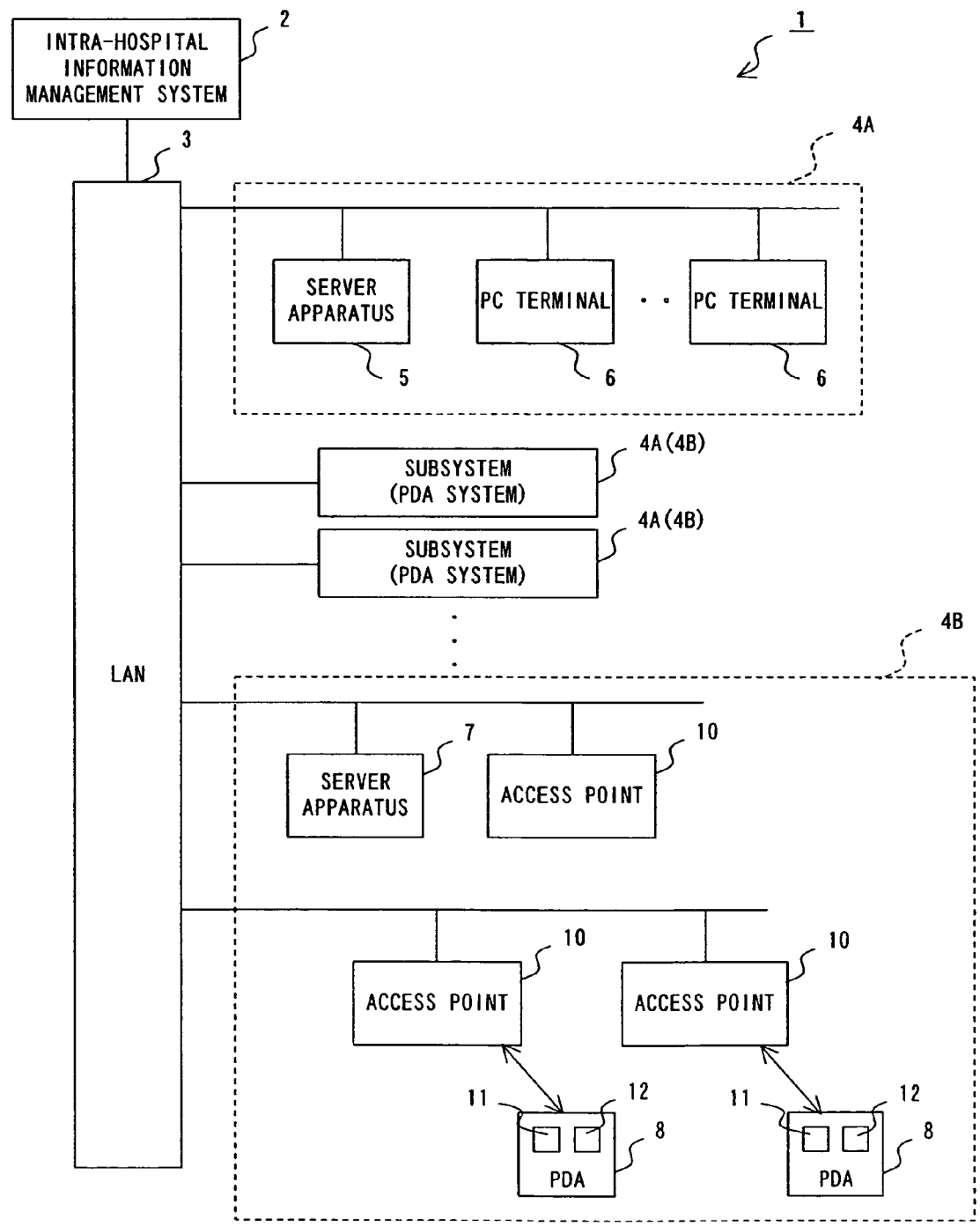
F I G. 1

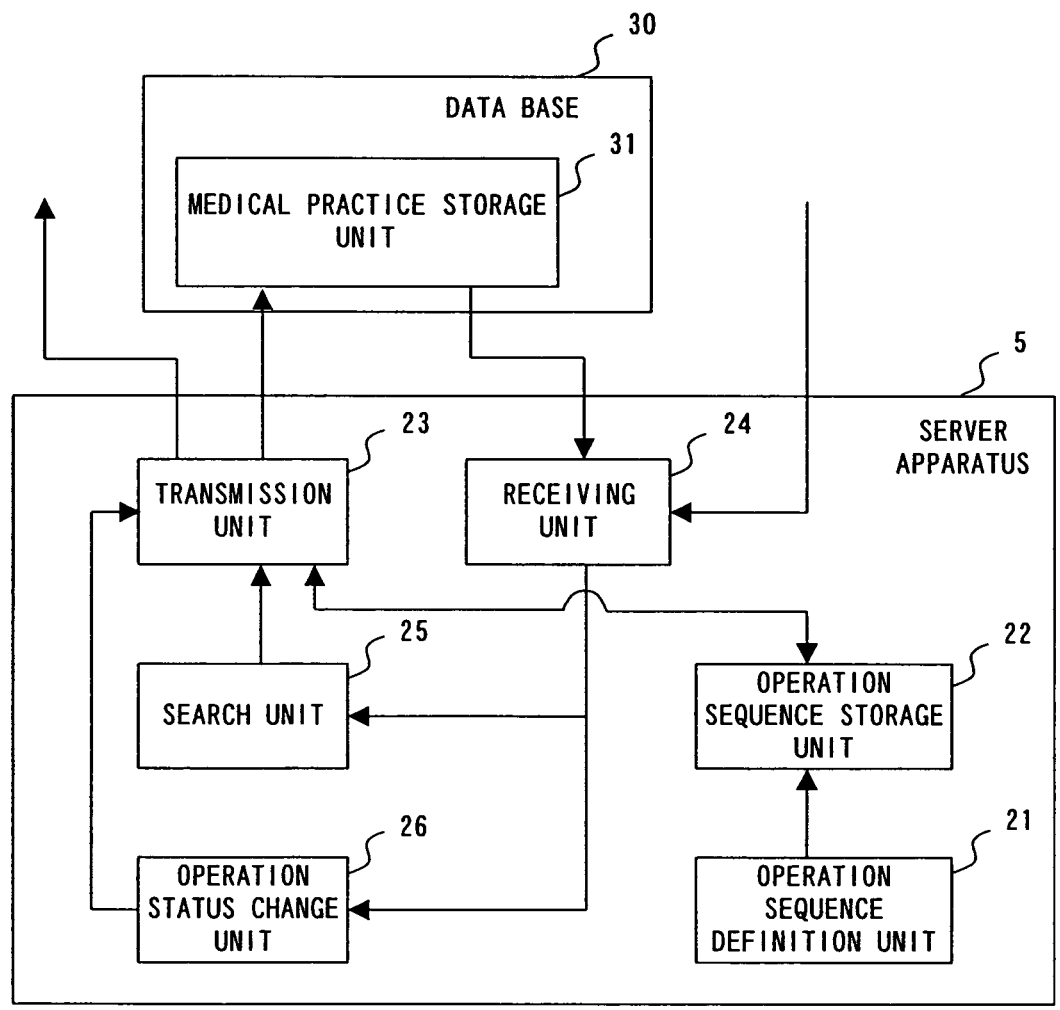
F I G. 2

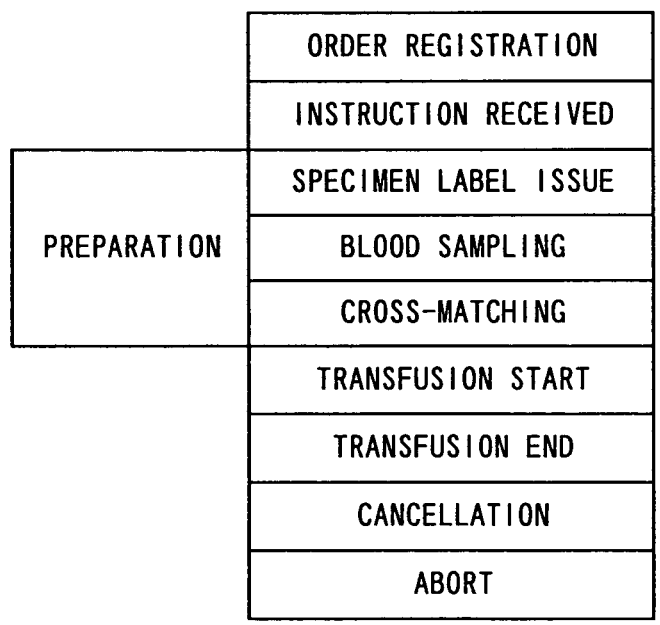
F I G. 5

| (TAG) STRUCTURE | WORK SCHEDULE DATA CONTENTS | OPERATION DATA CONTENTS |
|---|---|---|
| <PATIENT INFORMATION><br><ORDER CATEGORY><br><DISEASE NAME><br><REQUESTED PHYSICIAN><br><ATTENDING PHYSICIAN><br><WORK SCHEDULE DATA><br>　<PROGRESS><br>　<WORK ID><br>　<ORDER ID><br>　<WORK SCHEDULE DATE & TIME><br>　<OPERATION DATA><br>　　<KEY INFORMATION><br>　　<OPERATION DEPT.><br>　　<OPERATION PLACE><br>　　<PRACTICIAN><br>　　<OPERATION DATE & TIME><br>　　<OPERATION CONTENT><br>　　　<INSTRUCTION CONTENT><br>　　　　<OBJECT MATERIAL><br>　　　<OPERATION RATIONALE > | ID : 22222222 PATIENT B<br>TRANSFUSION ORDER<br>XXX<br>Dr. 〜<br>Dr. 〜<br>―<br>SCHEDULED<br>83924927998<br>29237629279<br>2002/06/05 10:00<br>―<br>RP-ID=023804734737931731<br>SURGERY<br>NORTH WARD 5F<br><br>TRANSFUSION START<br>ROUTE: PERIPHERAL VEIN<br>SPEED: XX ML/H<br>MAP A　Xml | ID : 22222222 PATIENT B<br>TRANSFUSION ORDER<br>XXX<br>Dr. 〜<br>Dr. 〜<br>―<br>OPERATION COMPLETED<br>83924927998<br>29237629279<br>2002/06/05 10:00<br>―<br>RP-ID=023804734737931731<br>SURGERY<br>NORTH WARD 5F<br>Ns〜<br>2002/06/05 10:04<br>TRANSFUSION START<br>ROUTE: PERIPHERAL VEIN<br>SPEED: XX ml/h<br>MAP A　Xml |

F I G. 6 A

| (TAG) STRUCTURE | WORK SCHEDULE DATA CONTENTS | OPERATION DATA CONTENTS |
|---|---|---|
| <PATIENT INFORMATION><br><ORDER CATEGORY><br><DISEASE NAME><br><REQUESTED PHYSICIAN><br><ATTENDING PHYSICIAN><br><WORK SCHEDULE DATA><br>  <PROGRESS><br>  <WORK ID><br>  <ORDER ID><br>  <WORK SCHEDULE DATE & TIME><br>  <OPERATION DATA><br>    <KEY INFORMATION><br>    <OPERATION DEPT.><br>    <OPERATION PLACE><br>    <PRACTICIAN><br>    <OPERATION DATE & TIME><br>    <OPERATION CONTENT><br>      <INSTRUCTION CONTENT><br>      <OBJECT MATERIAL><br>      <OPERATION RATIONALE> | ID : 22222222 PATIENT B<br>TRANSFUSION ORDER<br>XXX<br>Dr. ~<br>Dr. ~<br>―<br>SCHEDULED<br>83924927998<br>29237629279<br>2002/06/05 10:00<br>―<br>RP-ID=023804734737931731<br>SURGERY<br>NORTH WARD 5F<br>―<br>―<br>TRANSFUSION END<br>ROUTE: PERIPHERAL VEIN<br>SPEED: XX ML/H<br>MAP A  Xml<br>― | ID : 22222222 PATIENT B<br>TRANSFUSION ORDER<br>XXX<br>Dr. ~<br>Dr. ~<br>―<br>OPERATION COMPLETED<br>83924927998<br>29237629279<br>2002/06/05 10:00<br>―<br>RP-ID=023804734737931731<br>SURGERY<br>NORTH WARD 5F<br>Ns ~<br>2002/06/05 11:26<br>TRANSFUSION END<br>ROUTE: PERIPHERAL VEIN<br>SPEED: XX ml/h<br>ADMINISTERED: 100%<br>SIDE EFFECT: EVIDENT (a)<br>MAP A  Xml |

F I G. 6 B

```
CERTIFICATE OF CROSS-MATCHING
┌─────────────────────────────────┬──────────────────┐
│ PATIENT CHART NO. 0000001       │     0000001      │
├─────────────────────────────────┴──────────────────┤
│ NAME                                               │
│            A                                       │
├──────────────────────┬─────────────────────────────┤
│ BLOOD TYPE           │ IRREGULAR ANTIBODY          │
│         A+           │          (+)                │
├──────────────────────┴─────────────────────────────┤
│ SPECIALTY: CHILD MEDICINE                          │
└────────────────────────────────────────────────────┘

FORMULATION NAME:    RED CELL MAP 200
LOT NUMBER:          11-2610-0101
USE BY DATE          01 . 11 . 26
                                    CROSS-MATCH
MFG. BLOOD TYPE                      ┌──────┐
                                     │  A+  │
                                     └──────┘
INSPECTION DATE:    11 26 2001
```

F I G. 8 A

```
CERTIFICATE OF CROSS-MATCHING
```

| PATIENT CHART NO. 0000001 | 0000001 |
|---|---|
| NAME <br> A | |
| BLOOD TYPE <br> A+ | IRREGULAR ANTIBODY <br> (+) |
| SPECIALTY: CHILD MEDICINE | |

FORMULATION NAME:   RED CELL MAP 200

LOT NUMBER:   11-2610-0102

USE BY DATE   01 . 11 . 26

CROSS-MATCH

MFG. BLOOD TYPE   A+

INSPECTION DATE:   11 26 2001

FIG. 8B

| NOT DONE | DONE | |
|---|---|---|

| PAGE BACK | | PAGE FORWARD |
|---|---|---|

| DATE & TIME | PATIENT NAME | ITEM NAME |
|---|---|---|
| 24TH 09:00 | A | TRANSFUSION MAP |
| 24TH 09:00 | A | TRANSFUSION FFP |
| 24TH 09:30 | A | ELECTROLYTE INFUSION OF SOLITA |
| 24TH 10:00 | A | BODY TEMPERATURE |
| 24TH 10:00 | A | PULSE |

BACK

FIG. 10

ANY SIDE EFFECT OBSERVED?

⦿ EVIDENT   ○ NO   ○ UNKNOWN

IF "EVIDENT" REPORT SYMPTOMS OBSERVED

| | |
|---|---|
| a. | BODY TEMPERATURE RISE 1° C OR MORE |
| b | |
| c. | HIVES |
| d. | CHILL OR RIGOR |
| e. | NAUSEA OR VOMITING |
| f. | HEADACHE |
| g. | CHEST PAIN |
| h. | BREATHING DIFFICULTY |
| i. | BLOOD PRESSURE DECREASE |
| j. | ANAPHYLACTIC REACTION |
| k. | SHOCK |
| l. | HEMOLYTIC SYMPTOM |
| m. | HEMOGLOBINURIA |
| n. | OTHERS |

[ CANCEL ]     [ CONFIRM ]

F I G. 1 2

MEDICAL PRACTICE INFORMATION MANAGEMENT SYSTEM, MEDICAL PRACTICE OPERATION ASSISTANCE TERMINAL, MEDICAL PRACTICE INFORMATION MANAGEMENT METHOD, MEDICAL PRACTICE OPERATION ASSISTANCE METHOD, STORAGE MEDIA STORING MEDICAL PRACTICE INFORMATION MANAGEMENT PROGRAM AND STORAGE MEDIA STORING MEDICAL PRACTICE OPERATION ASSISTANCE PROGRAM

CROSS REFERENCE TO RELATED APPLICATIONS

This application is based upon and claims the benefit of priority from the prior Japanese Patent Application No. 2004-220268, filed Jul. 28, 2004, the entire contents of which are incorporated herein by reference.

BACKGROUND OF THE INVENTION

1. Field of the Invention

The present invention relates to a medical practice information management system for managing a medical practice such as blood transfusion operated for a patient and a medical practice operation assistance terminal such as mobile information terminal for use in the system.

2. Description of the Related Art

Various medical practices are provided for a patient in a hospital. Various systems are developed for assisting such medical practices.

As such a system, a system disclosed by a below noted patent document 1 configures a subsystem installed close to a hospital section (simply "section" hereinafter unless otherwise noted), where a medical practice is carried out, and enables to input information about the operation being completed through the subsystem.

[Patent document 1] Japanese patent application publication No. 2002-252064 "Hospital information system"

The system disclosed by the patent document 1 makes it possible to grasp a progress of medical practice, et cetera, in real time or semi-real time by installing a subsystem close to a section where the medical practice is carried out. Among medical practices, however, some are desired to be responsive to an order change relating to the medical practice for example as a result of referring to the medical practice prior to carrying out such as blood transfusion.

SUMMARY OF THE INVENTION

The challenge of the present invention is to provide a medical practice information management system and medical practice operation assistance terminal which make it possible to reflect an operation of medical practice in real time or semi-real time and respond to a content change thereof.

In a first aspect of the present invention, a medical practice information management system, for managing medical practice information through a medical practice information management apparatus exchanging data with one or more number of medical practice operation assistance terminals, wherein the medical practice information management apparatus comprises a medical practice storage unit for storing a medical practice carried out for a patient and a plurality of items constituting the aforementioned medical practice by correlating the former with the latter, a search unit for searching the stored medical practice based on information contained by a received acquisition request if the acquisition request for the stored medical practice is received, and a transmission unit for transmitting information about the search result performed by the search unit back to a sender of the acquisition request; and the medical practice operation assistance terminal comprises a medical practice acquisition unit which is capable of transmitting an acquisition request of a medical practice to the medical practice information management apparatus, and acquiring the medical practice(s) related to the acquisition request; a judgment unit comparing identifier of the readout item of a medical practice and identifier of the item specified among the displayed items of the acquired medical practice(s); and an acquisition decision maker unit for deciding whether or not the medical practice acquisition unit is to be activated with the specified item as search condition in accordance with a category of the specified item constituting the medical practice, if a readout identifier information identifies with the identifier information of the specified item.

In a second aspect of the present invention, a medical practice operation assistance terminal, capable of accessing a data base for managing information relating to a medical practice carried out for a patient, comprises a medical practice acquisition unit which is capable of transmitting an acquisition request of a medical practice to a data base storing information relating to medical practice(s), and acquiring the medical practice(s) related to the acquisition request; a judgment unit comparing identifier of the readout item of a medical practice and identifier of the item specified among the displayed items of the acquired medical practice(s); and an acquisition decision maker unit for deciding whether or not the medical practice acquisition unit is to be activated with the specified item as search condition in accordance with a category of the specified item constituting the medical practice, if a readout identifier information identifies with the identifier information of the specified item.

In a third aspect of the present invention, a medical practice information management method, in the method for managing medical practice information by a medical practice information management apparatus exchanging data with one or more number of medical practice operation assistance terminals, comprises the steps of the medical practice information management apparatus searching for a medical practice carried out for a patient within a data base accessible from a medical practice information management apparatus which stores the medical practice together with a plurality of items constituting the medical practice based on information contained by a received acquisition request, if the acquisition request for the stored medical practice is received from any one of the one or more number of the medical practice operation assistance terminals, and responding back to a transmitter of the acquisition request with information about the search result; and the medical practice operation assistance terminal acquiring a search result by making the medical practice information management apparatus search, by transmitting thereto an acquisition request relating to the stored medical practice, a plurality of items constituting the stored medical practice by a prescribed search condition contained by the acquisition request, displaying a list of acquired items constituting a medical practice or information based on acquired items constituting the medical practice in a display of the medical practice operation assistance terminal, comparing identifier information for identifying readout item constituting a medical practice with a responsible item within the medical practice specified as a part of the item list screen, and deciding whether or not the medical practice acquisition unit is to be activated as a specified item as search condition in accordance with a category of the specified item constituting a medical practice if readout identifier information identifies with identifier information contained by the specified item.

In a fourth aspect of the present invention, a medical practice operation assistance method, in the method for a computer assisting when carrying out a medical practice for a patient, comprises the steps of displaying in a screen a list of items constituting a medical practice acquired from a data base or information based on an acquired list constituting the medical practice in response to an acquisition request transmitted to an apparatus managing a data base which stores the medical practice and a plurality of items constituting the aforementioned medical practice by correlating the former with the latter; comparing identifier information about an item constituting a medical practice specified as a part of the item list screen with identifier information about an item constituting a medical practice which has been read out by way of an input unit; and deciding whether or not the acquisition request is to be transmitted to a management apparatus managing the data base so as to have each item constituting a medical practice stored in the data base searched by the specified item as search condition in accordance with a category of the specified item constituting a medical practice, if readout identifier information identifies with identifier information about the specified item.

In a fifth aspect of the present invention, a storage medium storing a program for making a computer manage information about a medical practice, wherein the program makes the computer carry out the steps of changing an operation status of a corresponding item within a storage unit of the computer which stores a medical practice carried out for a patient and a plurality of items constituting the medical practice by correlating the former with the latter to an "operation completed" based on a received information about "operation completed" which indicates that a prescribed item constituting the medical practice has been carried out; acquiring a search result by searching a medical practice stored by a storage unit of the computer by using a search condition contained by a received acquisition request for the medical practice or a search condition obtained from the acquisition request; and transmitting an acquired search result to an apparatus which is a transmitter of an acquisition request.

In a sixth aspect of the present invention, a storage medium storing a program for making a computer assist in carrying out a medical practice for a patient, wherein the program makes the computer carry out the steps of displaying, in a screen, a list of items constituting a medical practice acquired from the data base, or information based on acquired items constituting the medical practice in response to an acquisition request transmitted to an apparatus managing a data base which stores the medical practice and a plurality of items constituting the aforementioned medical practice by correlating the former with the latter; comparing identifier information about an item constituting a medical practice specified as a part of the item list screen with identifier information about an item constituting a medical practice which has been read out by way of an input unit; and deciding whether or not the acquisition request is to be transmitted to a management apparatus managing the data base so as to have each item constituting a medical practice stored in the data base searched by a specified item as search condition in accordance with a category of the specified item constituting the medical practice, if readout identifier information identifies with identifier information about the specified item.

The present invention enables a carried-out medical practice to be reflected to the data base storing the medical practice in real time or semi-real time. Furthermore, information relating to the specified item constituting the medical practice can be obtained by way of the acquisition decision maker unit prior to carrying out the medical practice, and therefore it is possible to respond to a content change thereof (i.e., order).

BRIEF DESCRIPTION OF THE DRAWINGS

FIG. 1 is an overall comprisal of medical services information management system according to an embodiment of the present invention;

FIG. 2 is a block diagram showing a comprisal of server apparatus in more detail as a subsystem capable of accessing a data base;

FIG. 5 exemplifies a group of items created in response to a blood transfusion order;

FIG. 6A exemplifies a data structure of XML file relating to items for starting a blood transfusion as per a blood transfusion order;

FIG. 6B exemplifies a data structure of XML file relating to items for ending a blood transfusion as per a blood transfusion order;

FIG. 8A exemplifies an issued formulation label (No 1);

FIG. 8B exemplifies an issued formulation label (No 2);

FIG. 10 exemplifies a screen display of an acquired medical practice;

FIG. 12 is a display example of registration screen for reporting a side effect.

DESCRIPTION OF THE PREFERRED EMBODIMENTS

Figure 3:
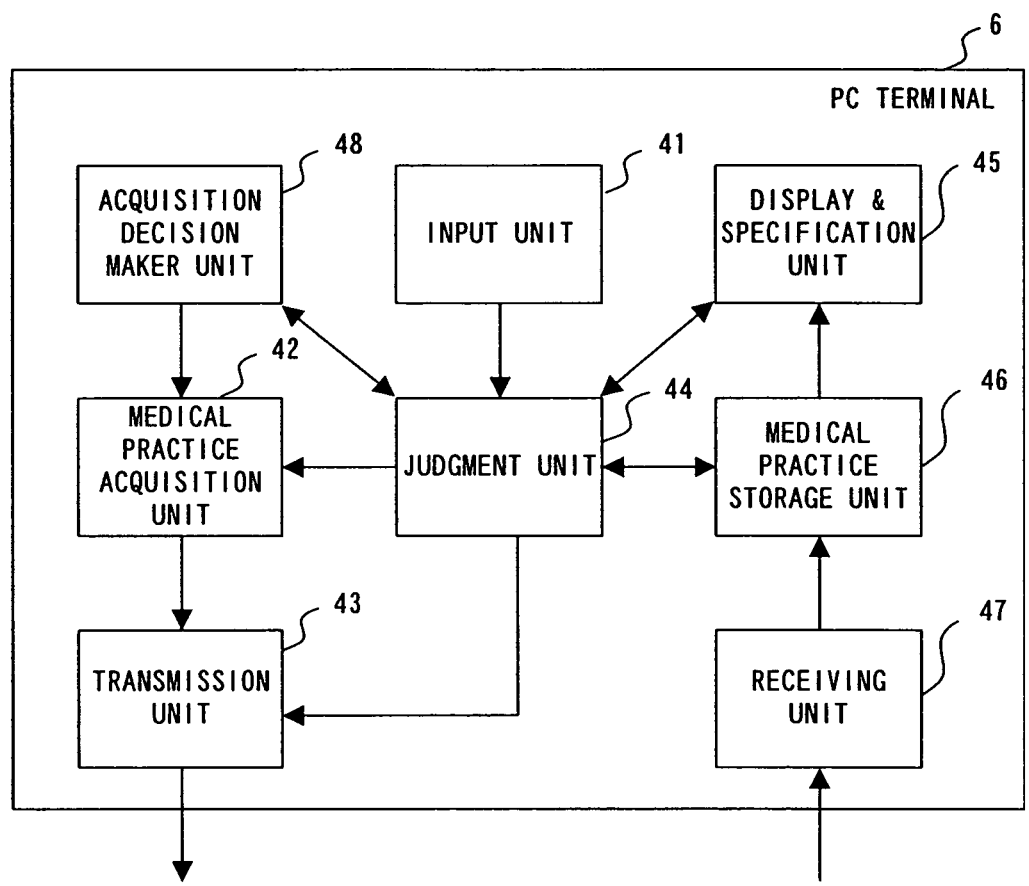
FIG. 3 is a block diagram showing a comprisal of PC terminal.

The following is a detailed description of the preferred embodiment of the present invention while referring to the accompanying drawings.

FIG. 1 is an overall comprisal of medical services information management system according to an embodiment of the present invention.

The medical services information management system 1 is installed in a medical facility such as a hospital and comprises an intra-hospital information management system 2 including an intra-hospital information management apparatus (not shown herein) capable of accessing a data base (not shown herein) which manages information relating to various medical practices carried out within the medical facility (i.e., hospital) and one or more number of subsystems 4A and 4B, respectively, which are connected with the intra-hospital information management system 2 by way of a network 3 for example and capable of renewing respective pieces of information relating to medical practices registered in the data base by accessing the data base within the intra-hospital information management system 2 by way of the network 3.

The above described data base stores each item constituting a medical practice created based on the inputted medical practice carried out for a patient by relating thereto.

Note that the present embodiment is configured to enable some of the subsystem, such as a server apparatus 5 constituting the subsystem 4A to access the data base, but can be configured differently so as to enable a server apparatus (i.e., intra-hospital information management apparatus), for example, constituting the intra-hospital information management system 2 to access the data base directly.

FIG. 2 is a block diagram showing a comprisal of server apparatus in more detail as a subsystem capable of accessing a data base.

In FIG. 2, the server apparatus 5 comprises an operation sequence definition unit 21 as a user interface capable of defining an operation sequence for each item of the above described medical practice. The user is enabled to define an operation sequence for the each item of medical practice stored by a medical practice storage unit 31 within a data base 30 by way of the operation sequence definition unit 21 comprised by the server apparatus 5. The defined operation sequence is stored by an operation sequence storage unit 22 by correlating with the corresponding medical practice.

Meanwhile, the server apparatus 5 is enabled to receive, by way of a receiving unit 24, "operation completed" information for indicating that a prescribed item within the medical practice has been carried out. In this event, an operation status change unit 26 changes the operation status of the relating item of the medical practice to "operation completed" based on the "operation completed" information.

Furthermore, the server apparatus 5 is enabled to receive, by way of a receiving unit 24, an acquisition request for a medical practice. In this event, a search unit 25 searches for a medical practice stored by the medical practice storage unit 31 by a search condition either contained by the received acquisition request or created based thereon to acquire a search result which is then transmitted to a transmitter of the search condition by a transmission unit 23.

Note that each PC terminal 6 subordinate to the server apparatus 5 has an operation assistance function for a medical practice.

The operation assistance function for a medical practice is largely categorized into the function of transmitting "operation completed" information to an apparatus managing the data base 30 so as to reflect the "operation completed" information thereon for indicating that an item within the medical practice for which the apparatus is responsible has been carried out, and that of querying whether or not a responsible item of the medical practice is to be carried out in terms of the above described sequence of operation.

FIG. 3 is a block diagram showing a comprisal of the PC terminal 6.

In FIG. 3, the PC terminal 6 comprises a medical practice acquisition unit 42 which has each item constituting a medical practice, that is stored by the data base 30 shown by FIG. 2 for example, searched by a prescribed search condition, and acquires the search result by way of a receiving unit 47; a medical practice storage unit 46 for storing the acquired medical practice; a display & specification unit 45 which makes a screen display a list of acquired medical practice items or information based on acquired medical practice items, and is capable of specifying a responsible item within the medical practice by designating a part of a screen displaying the list of items; an input unit 41 which is capable of reading out information for identifying each item constituting a medical practice; a judgment unit 44 for comparing inputted identifier information with identifier information contained by a specified item; an acquisition decision maker unit 48 for deciding whether or not the medical practice acquisition unit 42 is to be started up with the specified item as search condition in accordance with a category of the specified item constituting the medical practice, if the inputted identifier information identifies with the identifier information contained by the specified item; and a transmission unit 43 which is capable of transmitting "operation completed" information for indicating that the specified item has been carried out.

Incidentally, the input unit 41 is constituted by, for example, an identifier code reader for reading out an identifier code such as OCR printed on a medium as a subject of reading.

Respective items constituting a medical practice are largely categorized into practices requiring to be carried out on the patient's side and practices not requiring as such. For example, considering the case of blood transfusion (simply "transfusion" hereinafter unless otherwise noted) as an example of medical practice, the transfusion itself belongs to the former category, while a cross matching test, et cetera, belong to the latter.

In relation with FIG. 1, the subsystem 4A takes part in items not necessarily requiring an operation on the patient's side, while the subsystem 4B takes part in items carried out thereon, in the case of assisting an operation of medical practice. In either case, at least a part of these subsystems 4A and 4B is installed in, or close to, a place where the item constituting a medical practice will be carried out. This makes it possible to have a progress of the medical practice item reflected to the above described data base in real time or semi-real time.

Note that a stationary PC terminal 6 is usually used for the subsystem 4A, while a mobile information terminal (e.g., personal digital assistant; PDA) 8 is usually used for the subsystem 4B. The mobile information terminal allows a hand carry up to the patient's side, thereby enabling information relating to a medical practice carried out on the patient's side, such as a transfusion, to be reflected in the above described data base 30 in real time. Note also that an access point 10, used for the PDA 8 communicating with a server 7 which is included in the subsystem 4B to assist an operation of medical practice, is desirably installed in the neighborhood of the patients' room.

Figure 4:
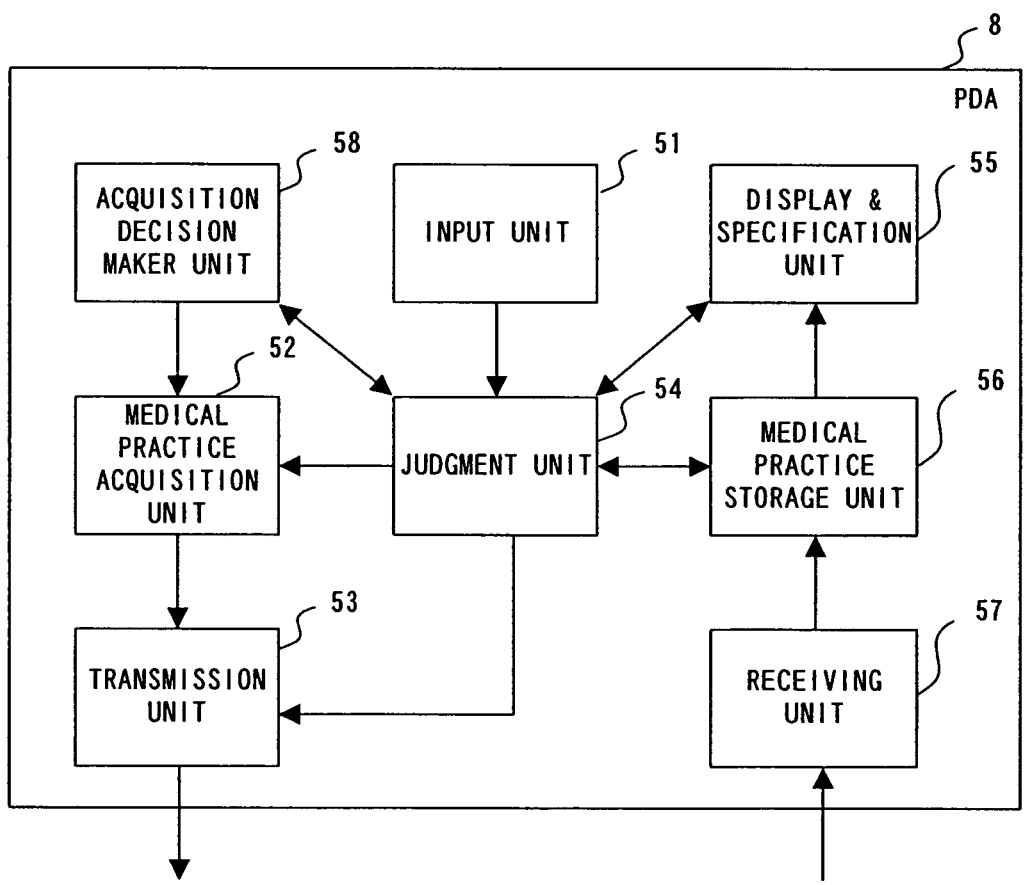
FIG. 4 is a block diagram showing a comprisal of PDA.

FIG. 4 is a block diagram showing a comprisal of the PDA 8.

In FIG. 4, the PDA 8 comprises a medical practice acquisition unit 52 which has each item constituting a medical practice, that is stored by the data base 30 shown by FIG. 2 for example, searched by a prescribed search condition, and acquires the search result by way of a receiving unit 57; a medical practice storage unit 56 for storing the acquired medical practice; a display & specification unit 55 which makes a screen display a list of acquired items constituting a medical practice or information based on acquired items constituting a medical practice, and is capable of specifying a responsible item within the medical practice by designating a part of a screen displaying the list of items; an input unit 51 which is capable of reading out information for identifying each item constituting a medical practice; a judgment unit 54 for comparing inputted identifier information with identifier information contained by a specified item; an acquisition decision maker unit 58 for deciding whether or not the medical practice acquisition unit 52 is to be activated with the specified item as search condition in accordance with a category of the specified item constituting the medical practice, if the inputted identifier information identifies with the identifier information contained by the specified item; and a transmission unit 53 which is capable of transmitting "operation completed" information for indicating that the specified item has been carried out.

Note that the transmission unit 53 and receiving unit 57 is comprised by a wireless LAN card 11 shown by FIG. 1 for example. And the input unit 51 is constituted by, for example, an identifier code reader 12 for reading out an identifier code such as OCR printed on a medium as a subject of reading.

Also note that the server 7 included in the subsystem 4B mainly transfers the above described "operation completed" information or query information to an apparatus in need of the information or an apparatus having information so as to enable its own apparatus to be capable of answering such query.

The following description deals with the case of carrying out a transfusion as a medical practice. Let it describe an example case of transfusion.

First, a physician issues a transfusion order to a transfusion department within the hospital as follows: "Make ready with three MAP (Mannitol Adenine Phosphate) s and one FFP (Fresh Frozen Plasma) for a surgery for the patient A."

Over at the transfusion dept., a responsible person places an order on the blood center, et cetera, for the specified formulation to obtain it, as well as registers the transfusion order with the data base 30 shown by FIG. 2. A responsible person also outputs a specimen label for identifying the transfusion order, sticks it onto a test tube and puts the blood sampled out of the patient A into the labeled test tube.

The obtained formulations from the manufacturer bear identifier numbers as follows:

MAP 12-3456-7890
MAP 12-3456-1112
MAP 12-3456-2222
FFP 12-3456-2000

A cross-matching of these formulations with the sampled blood is then conducted to produce a result as follows:

MAP 12-3456-7890: Passed a cross-matching
MAP 12-3456-1112: Passed a cross-matching
MAP 12-3456-2222: Failed a cross-matching
FFP 12-3456-2000: A cross-matching not required A decision is made based on the cross-matching result for carrying out a transfusion of the passed two MAPs and one not-required FFP.

An ensuing transfusion for the patient A in the patient's room (or surgical unit or hematological medicine dept.) obtains a result as follows:

MAP 12-3456-7890: 100% transfused
MAP 12-3456-1112: Not transfused due to a side effect
FFP 12-3456-2000: 100% transfused FIG. 5 exemplifies a group of items created in response to a blood transfusion order.

As shown by FIG. 5, once a transfusion is registered, a group of items constituting the transfusion order is created reactively. The group of items is made up of "order registration," "instruction received," "specimen label issue," "blood sampling," "cross-matching," "transfusion start," "transfusion end," "cancellation," and "abort."

The "order registration" is set as "complete" automatically when the transfusion order is registered, while the other items will be treated as "complete" when the operation status change unit 26 shown by FIG. 2 changes a data within the data base 30 as a result of receiving "operation completed" information from either the PC terminal 6 or PDA 8 shown by FIG. 1.

The received "operation completed" information contains criteria items, i.e., the practician, operation date & time, contents of operation items. And the criteria for dealing as "operation completed" or not is judged either based on whether or not respective data are entered for the above noted criteria items, i.e., practician, operation date & time, contents of operation items, or by referring to each "operation completed" flag which is attached to each of the above described criteria items.

The "instruction received" is treated as "complete" when an apparatus (not shown in FIG. 1) within a responsible section for receiving an instruction transmits a message about receiving the transfusion order as instruction thereto to an apparatus managing the data base.

The "specimen label issue" is treated as "complete" when a PC terminal 6 installed in the section issuing a specimen label for example transmits information about "a specimen label issued" to an apparatus managing the data base when issuing the specimen label as identifier information for identifying the transfusion order.

The "blood sampling" is treated as "complete" when a PC terminal 6 installed in the responsible section transmits a message about putting the blood sample taken from the patient into the test tube bearing the issued specimen label to an apparatus managing the data base.

The "cross-matching" is treated as "complete" when a PC terminal 6 installed in the responsible section for example transmits a message about carrying out a cross-matching of the drawing blood sample with each of formulations obtained from the respective manufacturers and obtaining all the results to an apparatus managing the data base.

The "transfusion start" is treated as "complete" when a PDA 8 transmits a message about starting a transfusion for the patient to an apparatus managing the data base.

The "transfusion end" is treated as "complete" when a PDA 8 transmits a message about ending a transfusion for the patient, which has already started, to an apparatus managing the data base.

When a responsible practician, such as a physician, who has issued a transfusion order canceling the transfusion order, she or he "cancels" it. The "cancellation" is carried out by a terminal of the responsible section transmitting the "cancellation" information to an apparatus managing the data base 30. And the apparatus managing the data base 30 receives the information and then the operation status change unit 26 shown by FIG. 2 changes the transfusion order so as to cancel it.

When a responsible practician, such as a physician, who has issued a transfusion order aborting the transfusion order, she or he "aborts" it. The "abortion" is carried out by a terminal of the responsible section transmitting the "abortion" information to an apparatus managing the data base 30. And the apparatus managing the data base 30 receives the information and then the operation status change unit 26 shown by FIG. 2 changes the transfusion order so as to abort it.

Incidentally, the "cancellation," and "abort" among the above described do not have any sequence of operation in relation with other items, as with the other items.

Each item constituting a medical practice order, such as a transfusion order, is created as a work schedule data at the time of registration. The work schedule data is created as a file in an XML structure for example, with a content of tag indicated by <progress> in the file being changed from "scheduled" to "operation completed" when the item is carried out.

FIG. 6A exemplifies a data structure of XML file relating to items for starting a blood transfusion as per a blood transfusion order; and FIG. 6B exemplifies a data structure of XML file relating to items for ending a blood transfusion as per a blood transfusion order.

In FIG. 6A, a tag <patient information> shows a patient ID with her/his name. And a tag <order category> shows a category of the order such as transfusion order. And a tag <order ID> shows an ID for identifying the order which has been given by the system at the time of the order registration. A tag <work ID> is an ID given to each work unit when the order is divided into the work units. For example, if a transfusion order is to transfuse the formulation pack of three MAPs and one FFP, a work ID can be assigned per formulation pack. A tag <operation content> specifies a name identifying an item within a medical practice, such as transfusion start. A tag <key information> varies with the item for medical practice entered into the tag <operation content> and, if the operation content is a transfusion start or end for example, specifies an ID for identifying a formulation pack to be transfused. That is, when the system outputs (i.e., issues) a formulation label to be attached to the formulation pack, the <key information> is overwritten with the same formulation ID.

A tag <instruction content> indicates a route and transfusion speed for the transfusion. And an <object material> specifies a kind of transfusing formula, such as MAP, FFP, et cetera.

The work schedule data shown by the second column of FIG. 6A will become operation data when carrying out, in which the tag <progress> changes to "operation completed," as described above, and the tags <practician> and <operation date & time> will be overwritten by the name of medical staff such as nurse and the date & time "06/05/2002 10:04" for example, respectively, at the same time.

FIG. 6B shows a data structure of the transfusion end file corresponding to the transfusion start shown by FIG. 6A. Due to this, the tags such as <work ID>, <key information>, <instruction content>, <object material> are set by the same ID. Likewise in the case of transfusion end, the work schedule data shown by the second column of FIG. 6B will become operation data when carrying out, in which the tag <progress> changes to "operation completed," as described above, and the tags <practician> and <operation date & time> will be overwritten by the name of medical staff such as nurse and the date & time "06/05/2002 11:26". And a tag <instruction content> is added by a portion of administration and a description about a presence or absence of side effect (i.e., "100% administered", "side effect": evident (a)"). Incidentally, the sign "a" in the parenthesis for the side effect corresponds to a later described sign shown by FIG. 12.

Figure 7A:
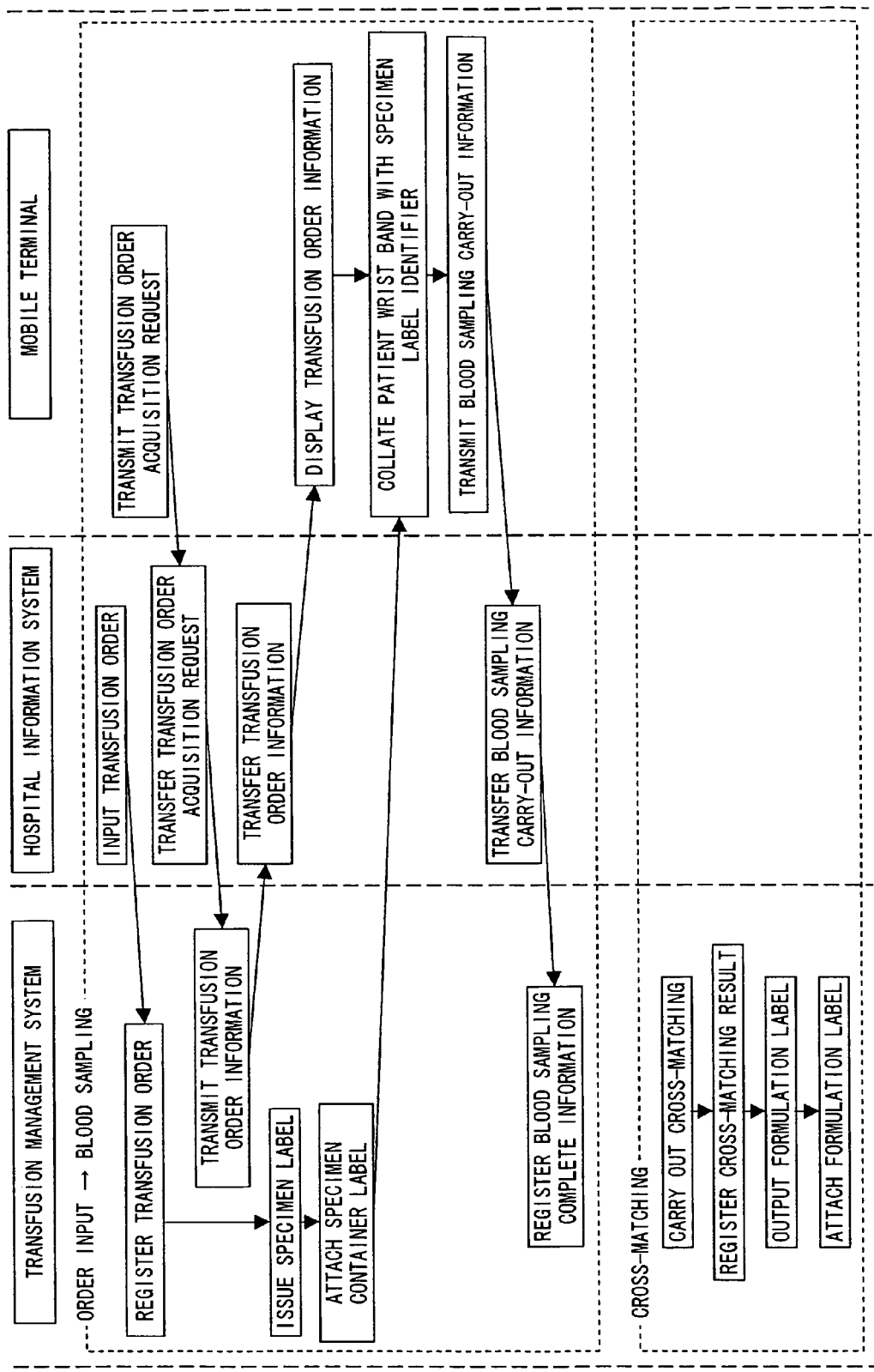
FIG. 7A is a sequence chart (No 1) exemplifying a processing carried out within a system in the case of specifying a blood transfusion order as a medical practice.
Figure 7B:
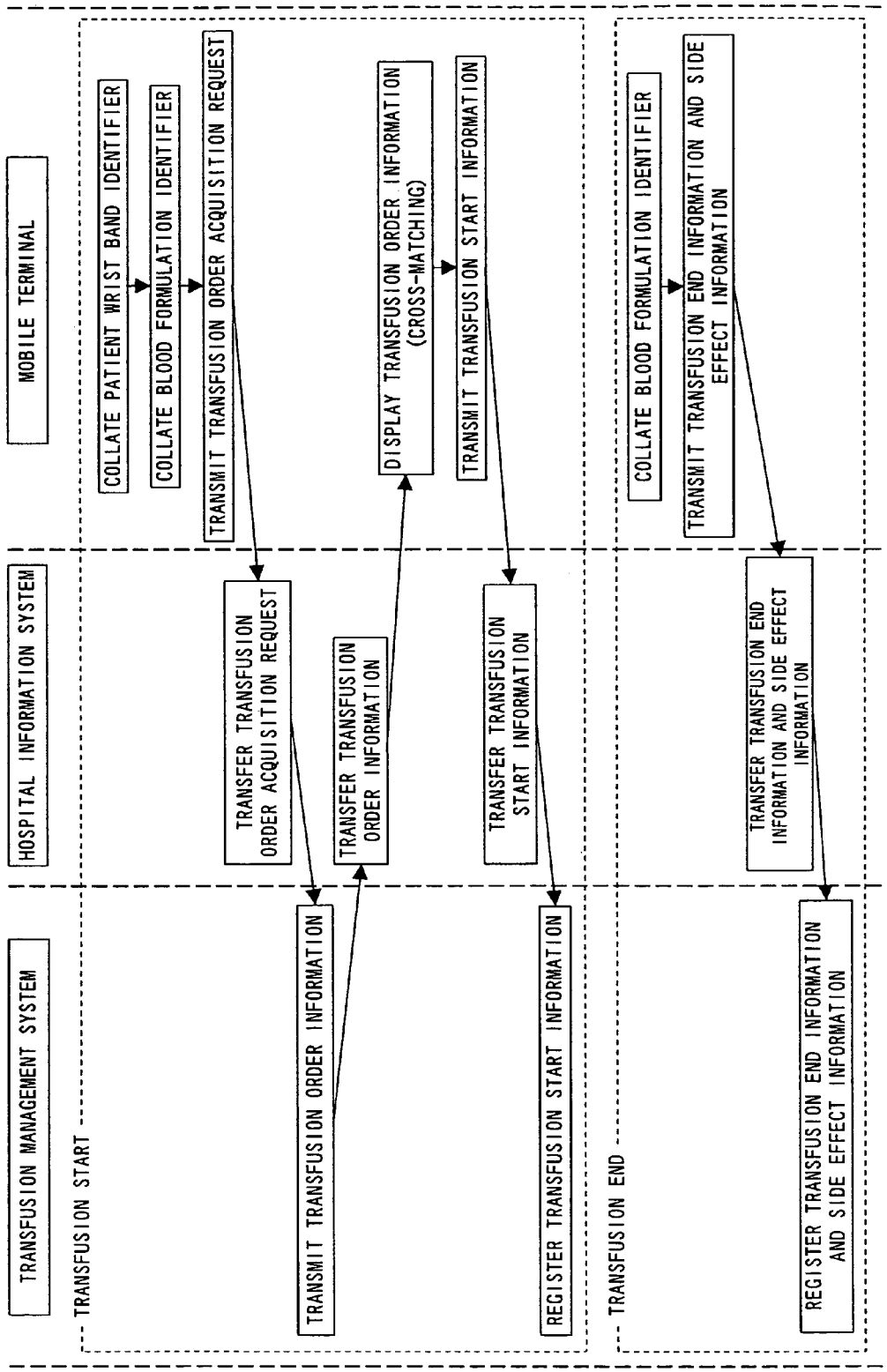
FIG. 7B is a sequence chart (No 2) exemplifying a processing carried out within a system in the case of specifying a blood transfusion order as a medical practice.

FIGS. 7A and 7B collectively is a sequence chart exemplifying a processing carried out within a system in the case of specifying a blood transfusion order as a medical practice.

In FIGS. 7A and 7B, a transfusion management system corresponds to the subsystem 4A shown by FIG. 1 for example, while a hospital information system corresponds to the intra-hospital information management system 2 shown by FIG. 1 for example. That is, the intra-hospital information management system 2 shown by FIG. 1 mainly carries out a transfer processing of data being exchanged among the subsystems, except for an input of transfusion order is done from a server apparatus or terminal within the system. Meanwhile, the subsystem 4A shown by FIG. 1 not only registers an inputted transfusion order but also creates a group of items corresponding to the transfusion order and stores, in a data base (e.g., data base 30 shown by FIG. 2), the created group of items by correlating with the transfusion order.

In FIG. 7A, first a terminal within the hospital information system inputs a transfusion order. In response to the input of the transfusion order, a server apparatus comprised by the transfusion management system receives the information by way of a server apparatus comprised by the hospital information system and so the information is stored in a data base (e.g., data base 30 shown by FIG. 2) directly accessible by the server apparatus.

Once the transfusion order is registered, the system gives identifier information thereto for identifying the transfusion order. Then a specimen label containing the identifier information is outputted (i.e., issued). The issued specimen label is then attached to a test tube in which will be put the sampled patient's blood. Information about the specimen label being issued is sent either from the server apparatus or PC terminal within the transfusion management system to the server apparatus therein as "operation completed" information. The operation status change unit 26 shown by FIG. 26 changes an operation status of the item corresponding to the medical practice (i.e., specimen label issue in this case) to an "operation completed" based on the "operation completed" information.

In FIG. 7A, meanwhile, a "transfusion order acquisition request" is transmitted, for example, to the server apparatus within the hospital information system over at the mobile terminal roughly in parallel with the above described processing in the transfusion management system. The server apparatus within the hospital information system receives the transfusion order acquisition request and transfers the transfusion order acquisition request to a section which has information relating to the transfusion order, such as a server apparatus within the transfusion management system.

Having received the transfusion order acquisition request, the server apparatus within the transfusion management system searches in the data base using a search condition for a medical practice either contained by the transfusion order acquisition request or created by a server apparatus within the transfusion management system, and acquires the search result.

The search condition maybe, for example, all items respectively constituting medical practices which are scheduled in a prescribed time after the clock time when the server apparatus within the transfusion management system received. Furthermore, it is also possible to narrow down the overall items constituting the medical practices scheduled to carry out by identifying a section which the apparatus transmitting the transfusion order acquisition request belongs to.

Incidentally, if a transmitter does not specify a search condition, the usual method is to acquire all the items constituting the medical practices around the clock time at which the acquisition request has been made, in consideration of the transmitting section; whereas, if the transmitter specifies a search condition so as to acquire data relating to transfusion order, such an acquisition request can be considered as a "transfusion order acquisition request".

The acquired search result is then received over at the mobile terminal (i.e., PDA) by way of a server apparatus within the hospital information system, followed by the display & specification unit 55 shown by FIG. 4 displaying in the screen of the mobile terminal.

Referring to FIG. 7A, following the above described display, the test tube bearing the specimen label (i.e., specimen container) is delivered up to the patient and a blood sampling is carried out as follows.

A responsible person such as a medical staff selects (i.e., specifies) an item relating to a blood sampling carried out for the patient from this point on, from among a list of not done items displayed in the screen of the mobile terminal.

By this specifying, the screen displays a message prompting to read a patient ID printed on the patient wrist band by using the input unit (e.g., identifier code reader) so that the medical staff reads it out according to the message. The judgment unit 54 shown by FIG. 4 then judges whether or not the patient ID read out by way of the input unit identifies with the patient ID included in the specified items out of the list in the screen.

If identification is made, the screen then displays a message prompting to let the input unit read an identifier ID identifying a transfusion order printed on the specimen label on the specimen container, the medical staff carries out the readout according to the message. The judgment unit 54 shown by FIG. 4 judges whether or not the transfusion order which has been read out by way of the input unit identifies with the transfusion order ID included in the specified items out of the list in the screen. If identification is made, a blood sampling is carried out for the patient, information about the carrying-out is transmitted to the server apparatus of the transfusion management system by way of the server apparatus of the hospital information system, as blood sampling operation information, in which the operation status change unit 26 shown by FIG. 2 reflects the information, in the data base, for indicating that the blood sampling has been carried out for the transfusion order.

Incidentally, when selecting (i.e., specifying) an item corresponding to the blood sampling carried out for the patient from this point on, from a list of not done items displayed in the screen of the mobile terminal, an item processing decision maker unit not shown by FIG. 4 considers whether or not a preceding item for the transfusion order has been carried out and, if any of the preceding items has not been carried out, displays a message indicating an inability of carrying out a blood sampling for the transfusion order in the screen of the mobile terminal.

Following the blood sampling, a cross-matching is carried out, which will be done in a section where the server apparatus or PC terminal of the transfusion management system is installed or nearby the section.

That is, a required formulation is delivered, a cross-matching is done by using the formulation and the sampled blood of the patient, a cross-matching result is registered in the data base upon finishing it and a formulation label to be attached onto each formulation pack is issued (i.e., outputted) at the same time for the registration. Note that the registration method for the cross-matching result is the same as in the case of the above described blood sampling.

FIGS. 8A and 8B exemplifies an issued formulation label. In this example, the applicable transfusion order corresponds to the case of transfusing at least two MAPs for the patient.

FIG. 8A shows a formulation label to be attached to a formulation pack with the formulation pack ID=11-2610-0101 for a patient of the patient ID=0000001. And FIG. 8B shows a formulation label to be attached to a formulation pack with the formulation pack ID=11-2610-0102 for the patient of the patient ID=0000001. That is, if one transfusion order uses a plurality of formulation packs, respective IDs are given thereto. This enables a finer management of transfusion process.

Figure 9:
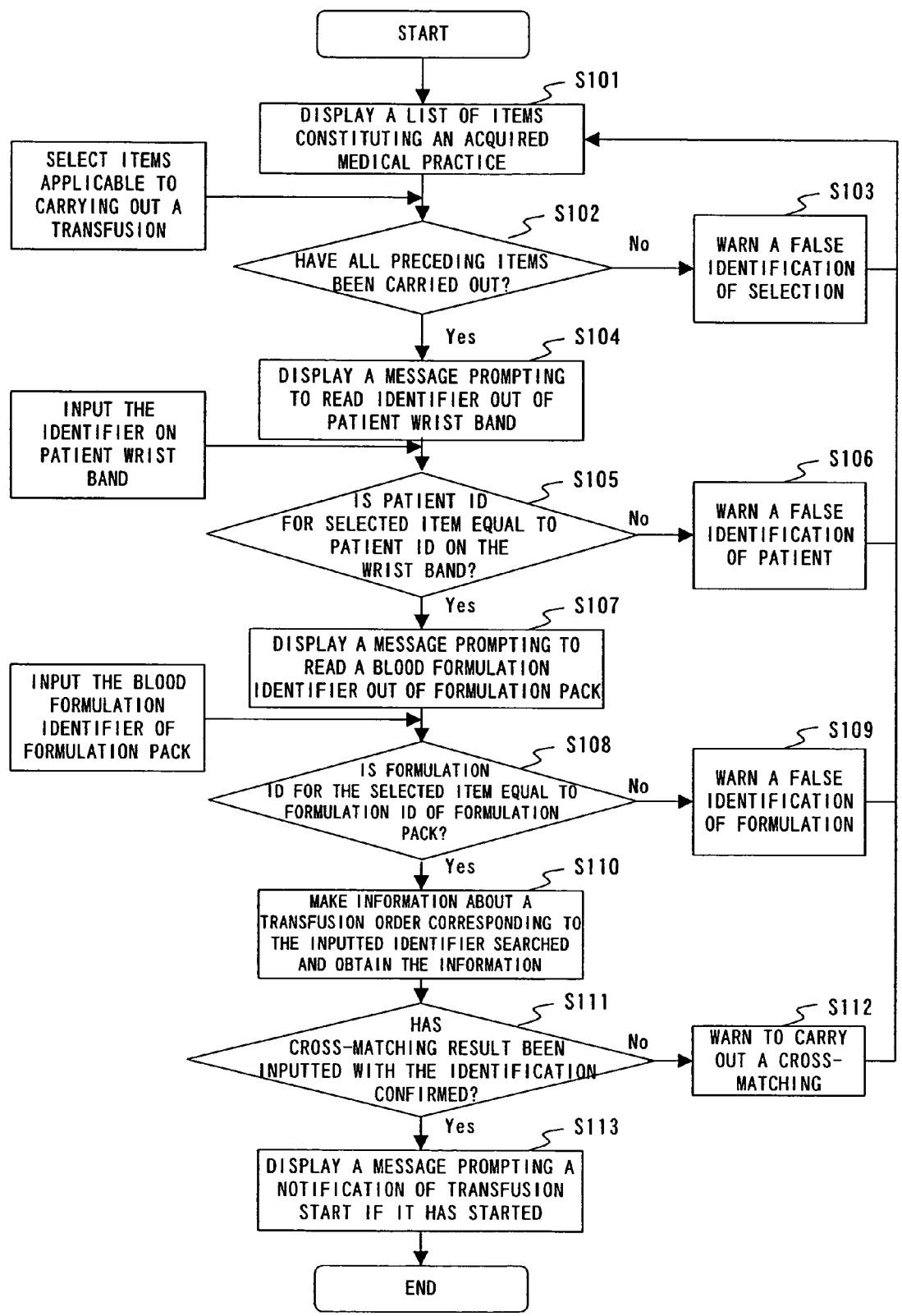
FIG. 9 is a flow chart showing a processing for carrying out a blood transfusion.

Now turning to the sequence chart shown by FIG. 7B, the description deals with the processing for starting a transfusion while referring to FIGS. 9 and 10.

FIG. 9 is a flow chart showing a processing for carrying out a blood transfusion.

In FIG. 9, first a screen of a mobile terminal displays a list of items constituting a medical practice including items for a transfusion order (step S101) (simply "S101" hereinafter).

FIG. 10 exemplifies a screen of mobile terminal displaying items relating to a transfusion order which has already been acquired by a transfusion order acquisition request and items for other medical practice which is already acquired. In this screen display, those items yet to be carried out are the subject of display, with each item being displayed in sequence of operation for example.

A medical staff such as a nurse selects the items applicable to carrying out a transfusion for the transfusion order, such as a transfusion MAP, prior to carrying out a transfusion for the patient as per the transfusion order.

When an item applicable to carrying out a transfusion is selected (i.e., specified) (assumption here is that the list which has been already acquired through the above described "transfusion order" acquisition request contain items applicable to carrying out a transfusion as shown by FIG. 10) from the list, the item processing decision maker unit, reactive to the specifying, checks whether or not all the items preceding the transfusion order are completed (S102). If all the preceding items are not completed, the screen of the mobile terminal displays a message about selecting the transfusion MAP not being appropriate (S103).

On the other hand, if all the preceding items are completed, the screen display changes to prompt reading out identifier information indicating a patient ID which is printed on the patient wrist band (S104).

As the medical staff reads the identifier information out of the patient wrist band, the judgment unit 54 shown by FIG. 4 collates a patient ID included in the selected transfusion MAP with the readout patient ID (S105).

If the patient ID included in the selected transfusion MAP does not identify with the readout patient ID, the screen displays a message warning a false identification of patient (S106). On the other hand, if the patient ID included in the selected transfusion MAP identifies with the readout patient ID, the screen displays a message to prompt to read out identifier information (ID) of blood formulation, which is attached to the formulation pack (S107).

As the medical staff reads the identifier information (of the blood formulation) out of the label attached to the formulation pack, the judgment unit 54 shown by FIG. 4 collates the blood formulation ID included in the selected transfusion MAP with the blood formulation ID on the readout label of the formulation pack (S108).

If the blood formulation ID included in the selected transfusion MAP does not identify with the blood formulation ID on the readout label of the formulation pack, the screen displays a message warning a false identification of formulation (S109).

On the other hand, if the blood formulation ID included in the selected transfusion MAP identifies with the blood formulation ID on the readout label of the formulation pack, the acquisition decision maker unit 58 shown by FIG. 4 activates the medical practice acquisition unit 52 and instructs it to transmit the information instructing the server apparatus of the transfusion management system so as to search information about a transfusion order corresponding to the readout identifiers (i.e., patient ID and blood formulation ID) form the database, and acquires the search result (S110).

Then, referring to the search result, the judgment unit 54 shown by FIG. 4 checks whether or not a cross-matching is carried out and therefore the test result thereof has already been inputted to the data base and the test result has confirmed a "cross-match" with the blood sampled from the patient (Sill).

If the check has produced a result such as a cross-matching test result not inputted, no cross-match, et cetera, the screen displays a message prompting to carry out a cross-matching (S112).

On the other hand, if a cross-matching is already done, with the result having been inputted and a cross-match having been confirmed, then the screen displays, along with a transmission button to be pressed when a transfusion is started, a message prompting to start the transfusion (S113).

Incidentally, while the flow chart shown by FIG. 9 does not make it apparent, there is usually a step between the steps S108 and S110 in which the acquisition decision maker unit 58 shown by FIG. 4 decides whether or not information about corresponding medical practice relating to the selected (i.e., specified) item shall be acquired depending on the category of the selected item. For example, in the case of transfusion order, the decision is not to be acquired for the item of blood sampling, while the decision is to be acquired for the item of carrying out a transfusion (i.e., start). Such decision by the acquisition decision maker unit 58 is done, for example, based on a medical practice acquisition flag which is set for each item constituting a medical practice. Such an acquisition decision maker function can of course be furnished over in the PC terminal shown by FIG. 6 for example.

Such configuration enables a medical staff, et al, to comprehend the information about a medical practice prior to carrying out the medical practice such as transfusion, hence responsive to an order change relating to the medical practice as well.

Going back to FIG. 7B again, such transmitted "transfusion start information" is transmitted, by way of the server apparatus of the hospital information system, to the server apparatus of the transfusion management system and registered in the data base therein.

Note that the present embodiment is configured to manage a transfusion start and end for each pack of blood formulation in order to manage an operation process of transfusion more finely. This will require managing a transfusion start and end for each formulation pack in the case of one transfusion order consisting of transfusing two MAPs and one FFP in sequence for example.

In the sequence chart shown by FIG. 7B, noted is a processing done at the time of ending a transfusion for the formulation pack with which the transfusion has started.

That is, identifier information of the blood formulation is read by way of the input unit at a transfusion end. The judgment unit 54 shown by FIG. 4 judges whether or not a blood formulation corresponding to the read identifier information is in fact the one with which the transfusion started.

If it is not the one with which the transfusion started, the judgment unit 54 lets the screen of the mobile terminal display a message warning a false identification of formulation pack. Meanwhile, if it is the one with which the transfusion started, a transfusion end information & side effect report is transmitted, by way of the server apparatus of the hospital information system, to the server apparatus of the transfusion management system, and registered in the data base comprised thereby.

FIG. 12 exemplifies registration items for a side effect report. The screen of the mobile terminal displays the content shown by FIG. 12 so as to input a presence or absence and symptom of the side effect.

According to the present invention, a progress of medical practice is reflected to the data base as a result of the medical practice information management apparatus and medical practice operation assistance terminal exchanging "operation completed" information for example as described above, and in particular the reflection in the data base can be done in real time or semi-real time as a result of installing the medical practice operation assistance terminal close to a section where the items constituting the medical practice, or moving close thereto. Furthermore, information relating to the specified items constituting a medical practice can be acquired by way of the acquisition decision maker unit prior to carrying out the medical practice, hence enabling a response to a content change of the medical practice (i.e., order).

Figure 11:
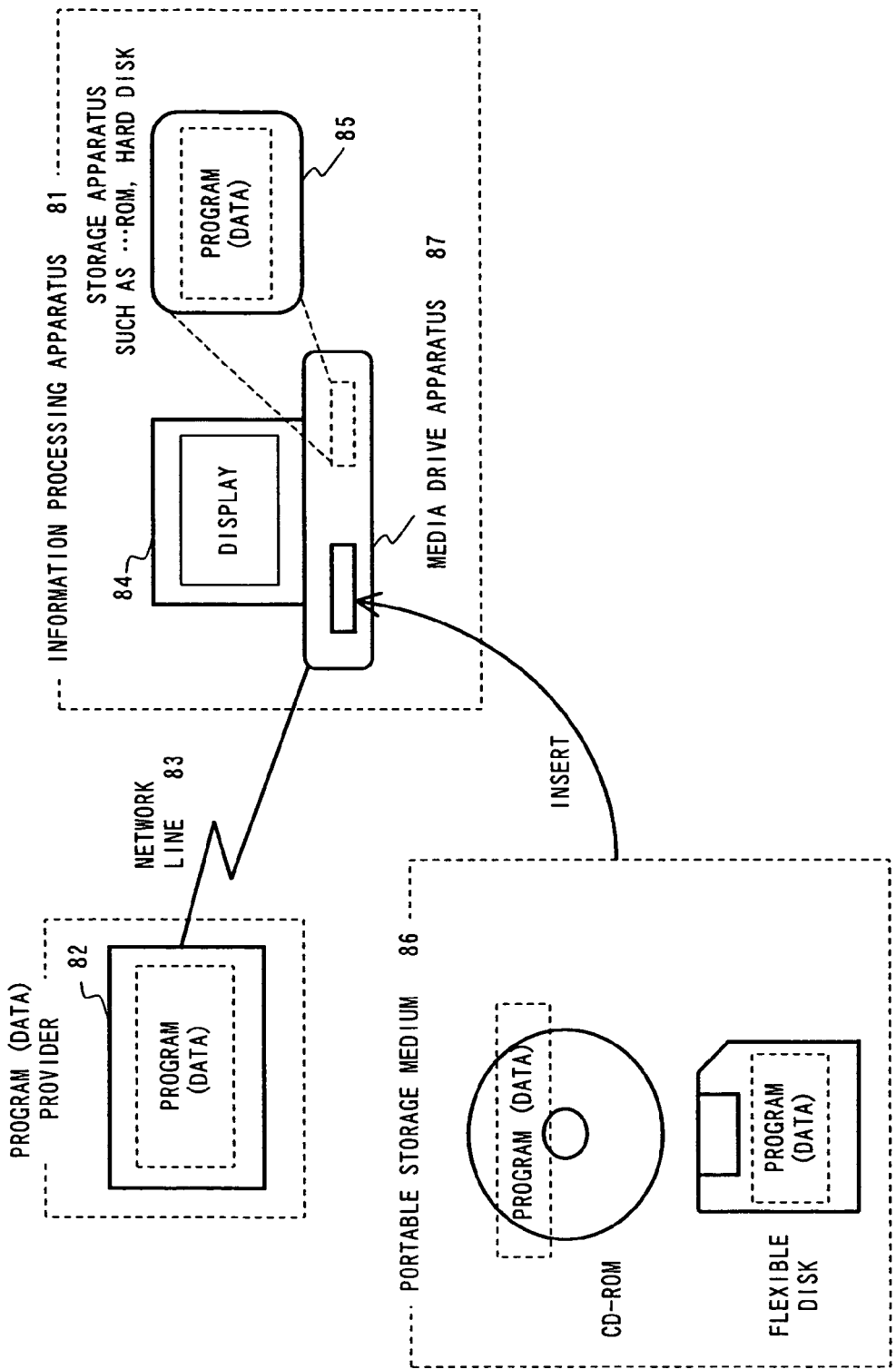
FIG. 11 exemplifies a storage medium.

FIG. 11 exemplifies a storage medium for storing a program to make a computer execute each processing according to the present embodiment.

As shown by FIG. 11, the above noted storage medium comprehends a portable storage medium 86 which is detachably attachable to a media drive apparatus 87 accepting a CD-ROM, flexible disk (that may include an MO, DVD, removable hard disk, et cetera), et cetera, a storage unit (such as a database) 82 within an external apparatus (such as a server) which transmits the program by way of a network line 83, and a memory (such as a RAM or hard disk) 85 within a main body 84 of information processing apparatus 81. The program for carrying out each processing according to the present embodiment, such as the one for accomplishing various judgment processings carried out by the judgment unit 44 shown by FIG. 3 or the judgment unit 54 shown by FIG. 4, is loaded from the above noted storage medium onto the memory 85 within the main body 84 so as to be executed.

What is claimed is:

1. A medical procedure information management system, for managing medical procedure information comprises:
   a medical procedure information management apparatus including:
      a medical procedure storage unit configured and operable for storing a plurality of items constituting a medical procedure carried out for a patient with an operation sequence of the plurality of items in association with the medical procedure,
      a search unit configured and operable for searching the medical procedure storage unit for at least stored information regarding the medical procedure based on information contained by a received acquisition request after the acquisition request for the stored medical procedure is received, and
      a transmission unit configured and operable for transmitting information about a search performed by the search unit back to a sender of the acquisition request; and
   a medical procedure operation assistance terminal, configured to perform the following steps:
      transmit the acquisition request to the medical procedure information management apparatus, and to acquire the information about the search related to the medical procedure related to the acquisition request;
      determine when a certain item of the medical procedure is specified from an obtained list of items of the medical procedure and whether all items of the medical procedure preceding the specified item have been carried out,
      when it is determined that all the preceding items that precede the specified item have been carried out, compare an identifier of a readout item of a medical procedure to be performed and an identifier of the specified item specified from among displayed items related to the acquired medical procedure; and
      decide whether the medical procedure acquisition unit is to be activated with the specified item of the medical procedure, when the identifier of the readout item matches with the identifier information of the specified item.

2. The medical procedure information management system according to claim 1, wherein said medical procedure information management apparatus is further configured to receive "operation completed" information indicating that a prescribed item constituting the medical procedure has been carried out, and to change an operation status of an applicable item within the medical procedure to "operation completed" based on the "operation completed" information, and said medical procedure operation assistance terminal further comprises a transmission unit for transmitting the "operation completed" information indicating that said specified item has been carried out.

3. The medical procedure information management system according to claim 2, including activating said transmit step when the specified item is used to carry out a blood transfusion.

4. The medical procedure information management system according to claim 2, wherein said "operation completed" information contains information related to a practician, operation date and time and content of the operation item performed.

5. The medical procedure information management system according to claim 1, including activating said transmit step when the specified item is used to carry out the medical procedure.

6. The medical procedure information management system according to claim 1, including determining whether an applicable medical procedure has been carried out by checking whether data indicating the practician, operation date and time and content of the operation performed have been entered.

7. The medical procedure information management system according to claim 1, including determining whether an applicable medical procedure has been carried out by checking an "operation completed" flag associated with each completed item indicating whether the item has been carried out.

8. The medical procedure information management system according to claim 1, wherein said medical procedure operation assistance terminal is a non-portable terminal installed in the vicinity of an item for which it is responsible.

9. The medical procedure information management system according to claim 1, wherein said medical procedure operation assistance terminal is a mobile information terminal taking responsibility for an item carried out next to said patient.

10. A medical procedure information management system, for managing medical procedure information comprises:

a medical procedure information management apparatus including:
a medical procedure storage unit configured and operable for storing each item constituting a medical procedure for a patient and correlating each item with the medical procedure, and a processor configured to carry out the following steps:
defining a sequence of operating including each item constituting the medical procedure,
storing a defined operation sequence provided by the operation sequence definition unit,
receiving "operation completed" information from at least one medical procedure operation assistance terminal indicating that a prescribed item constituting a medical procedure has been carried out,
changing an operation status of an applicable item of the medical procedure to "operation completed" based on the "operation completed" information,
receiving an acquisition request for the medical procedure from the at least one medical procedure operation assistance terminal, and
searching the storage unit for the stored medical procedure by a search condition contained in a received acquisition request or by a search condition obtained therefrom, and a transmission unit for transmitting information about the search performed by the search unit back to a transmitting source terminal of the acquisition request;

wherein the medical procedure operation assistance terminal, configured to perform the steps of:
making the medical procedure information management apparatus search, by transmitting thereto the acquisition request, with each item constituting the stored medical procedure identified by a prescribed search condition, and to acquire the search result,
displaying on a screen visible to a user, a list of acquired items constituting a medical procedure or information based on acquired items constituting the medical procedure included in the search result, and specifying a responsible item within the medical procedure by designating a part of a screen displaying the list of items that includes the responsible item,
determining whether all items of the medical procedure preceding the specified item have been carried out,
determining that all the preceding items have been carried out, of reading out identifier information for identifying each item constituting a medical procedure,
comparing inputted identifier information with identifier information contained by the specified item,
deciding to activate the making step when the inputted identifier information matches with the identifier information contained by the specified item, and
transmitting "operation completed" information for indicating that the specified item has been carried out.

11. A medical procedure operation assistance terminal, configured and operable to access a data base for managing information relating to at least one medical procedure carried out for a patient, comprising:
a medical procedure acquisition unit configured and operable for transmitting an acquisition request of a medical procedure to the data base storing information relating to the medical procedure, and acquiring information relating to the medical procedure related to the acquisition request;
a judgment unit configured and operable for comparing an identifier of the readout item of a medical procedure and an identifier of a specified item among displayed items included in the acquired information relating to the medical procedure;
an acquisition decision maker unit configured and operable for deciding that the medical procedure acquisition unit is to be activated with the specified item of the medical procedure, when a readout identifier information matches with identifier information of the specified item;
wherein said data base stores a plurality of items constituting said medical procedure and also an operation sequence of the plurality of items, and
an item processing decision maker unit configured and operable for deciding that the processing of the specified item constituting a medical procedure is allowable when all items preceding the specified item in medical procedure have been carried out.

12. The medical procedure operation assistance terminal according to claim 11, wherein said data base stores the at least one medical procedure carried out for a patient and a plurality of items constituting the aforementioned medical procedure and correlates the former with the latter.

13. The medical procedure operation assistance terminal according to claim 11, wherein said acquisition decision maker unit activates the medical procedure acquisition unit when the specified item is utilized for carrying out the medical procedure.

14. The medical procedure operation assistance terminal according to claim 11, wherein said acquisition decision maker unit activates the medical procedure acquisition unit when the specified item is utilized for carrying out a blood transfusion.

15. The medical procedure operation assistance terminal according to claim 11, wherein said "operation completed" information indicates a practician, operation date and time and content of operation item performed.

16. The medical procedure operation assistance terminal according to claim 11, wherein said medical procedure operation assistance terminal is a non-portable terminal installed in the vicinity of an item for which it is responsible.

17. The medical procedure operation assistance terminal according to claim 11, wherein said medical procedure operation assistance terminal is a mobile information terminal taking responsibility for an item carried out next to said patient.

18. A medical procedure operation assistance terminal, configured and operable to access a data base for managing information relating to a medical procedure carried out for a patient, comprising:
  a medical procedure acquisition unit configured and operable for making a management apparatus that manages the data base search, by transmitting thereto an acquisition request relating to at least one stored medical procedure in the data base, for a plurality of items constituting the stored medical procedure by a prescribed search condition contained in the acquisition request, and to acquire a search result from the data base;
  a display and specification unit configured and operable to display a list of acquired items constituting the medical procedure or information based on acquired items constituting the medical procedure, and specifying a responsible item within the medical procedure by designating a part of a screen displaying the list of items including the responsible item;
  an item processing decision maker configured and operable to determine whether all items of the medical procedure preceding the specified item have been carried out,
  an input configured and operable for performing a process, when the item processing decision maker unit determines that all the preceding items of the medical procedure have been carried out, of reading out information identifying each item constituting a medical procedure performed;
  a judgment module for comparing readout identifier information from the input unit with identifier information contained in the specified item when the item processing decision making unit determines that all the preceding items of the medical procedure preceding the specified item have been carried out;
  an acquisition decision maker configured and operable for deciding that the medical procedure acquisition unit is to be activated with the specified item as a search condition in accordance with a category of the specified item constituting the medical procedure, when the readout identifier information matches with the identifier information contained in the specified item; and
  a transmission module configured and operable for transmitting "operation completed" information indicating that the specified item has been carried out.

19. A medical procedure information management method comprising the steps of:
  searching a medical procedure information management apparatus for a medical procedure carried out for a patient within a data base accessible from the medical procedure information management apparatus which stores the medical procedure together with a plurality of items constituting the medical procedure and an operation sequence of the plurality of items based on information contained by a received acquisition request from any one of one or more medical procedure operation assistance terminals,
  responding back to a transmitter of the acquisition request with information about the search result;
  acquiring at the medical procedure operation assistance terminal the search result after making the medical procedure information management apparatus search, by transmitting thereto an acquisition request relating to the stored medical procedure, including a plurality of items constituting the stored medical procedure by a prescribed search condition contained by the acquisition request,
  displaying a list of acquired items constituting a medical procedure or information based on acquired items constituting the medical procedure in a display of the medical procedure operation assistance terminal,
  specifying a certain item of the list of acquired items;
  determining whether all items preceding the specified item on the list of acquired items have been carried out,
  comparing identifier information for an item constituting a medical procedure performed with a responsible item within the medical procedure specified as a part of the list when all items preceding the specified item on the list of acquired items have been carried out, and
  deciding that the medical procedure acquisition unit is to be activated by a specified item as a search condition in accordance with a category of the specified medical procedure item when the readout identifier information matches with identifier information contained in the specified item.

20. A medical procedure operation assistance method comprising the steps of:
  displaying in a screen a list of items constituting a medical procedure acquired from a data base or information based on an acquired list constituting the medical procedure in response to an acquisition request transmitted to an apparatus managing a data base which stores the medical procedure and a plurality of items constituting the aforementioned medical procedure and an operational sequence of the plurality of items by correlating the former with the latter;
  specifying a certain item of the list of items;
  determining whether all items preceding the specified item on the list of items have been carried out;
  comparing identifier information about the specified item as a part of the item list on the screen with identifier information about an item constituting a medical procedure to be performed which has been read out by way of an input unit; and
  deciding whether the acquisition request is to be transmitted to a management apparatus managing the data base so as to have each item constituting a medical procedure stored in the data base searched by the specified item as search condition in accordance with a category of the specified item constituting a medical procedure, when readout identifier information matches with identifier information about the specified item.

21. A computer readable storage medium storing a computer program product for managing information about a medical procedure, wherein the computer program product comprises program segments that when executed on a computer causes the computer to carry out the steps of:

changing an operation status of a corresponding item within a storage unit of the computer which stores a medical procedure carried out for a patient and a plurality of items constituting the medical procedure with an operation sequence of the plurality of items by correlating the former with the latter to an "operation completed" based on a received information about "operation completed" which indicates that a prescribed item constituting the medical procedure has been carried out;

acquiring a search result by searching a medical procedure stored by a storage unit of the computer by using a search condition contained by a received acquisition request for the medical procedure or a search condition obtained from the acquisition request; and transmitting an acquired search result to an apparatus which is a transmitter of an acquisition request.

22. A computer readable storage medium storing a computer program product for carrying out a medical procedure for a patient, wherein the program product comprises program segments that when executed on a computer makes the computer carry out the steps of:

displaying, in a screen, a list of items constituting a medical procedure acquired from the data base, or information based on acquired items constituting the medical procedure in response to an acquisition request transmitted to an apparatus managing a data base which stores the medical procedure and a plurality of items constituting the aforementioned medical procedure with an operation sequence of the plurality of items by correlating the former with the latter;

specifying an item of the list of items;

determining whether all items preceding the specified item have been carried out;

comparing identifier information about the specified item as a part of the item list on the screen with identifier information about an item constituting a medical procedure which has been read out by way of an input unit when all items preceding the specified item have been carried out; and deciding whether the acquisition request is to be transmitted to a management apparatus managing the data base so as to have each item constituting a medical procedure stored in the data base searched by the specified item as search condition in accordance with a category of the specified item constituting the medical procedure, when readout identifier information identifies with identifier information about the specified item.

23. The computer readable storage medium according to claim 22, further comprising deciding to acquire a search result in said deciding step when the specified item constituting a medical procedure is an item relating to carrying out the medical procedure.

* * * * *